United States Patent
Miura et al.

(10) Patent No.: US 7,611,737 B2
(45) Date of Patent: Nov. 3, 2009

(54) ANTIWRINKLE AGENT AND SKIN COSMETIC COMPOSITION

(75) Inventors: Kyoko Miura, Kanagawa (JP); Akinori Haratake, New York, NY (US); Syunsuke Yamazaki, Kanagawa (JP); Bunichi Okabe, Kanagawa (JP); Takeshi Ikemoto, Kanagawa (JP)

(73) Assignee: KAO Corporation, Tokyo (JP)

( * ) Notice: Subject to any disclaimer, the term of this patent is extended or adjusted under 35 U.S.C. 154(b) by 138 days.

(21) Appl. No.: 11/579,094

(22) PCT Filed: Apr. 28, 2005

(86) PCT No.: PCT/JP2005/008112

§ 371 (c)(1),
(2), (4) Date: Oct. 30, 2006

(87) PCT Pub. No.: WO2005/105019

PCT Pub. Date: Nov. 10, 2005

(65) Prior Publication Data

US 2007/0231416 A1    Oct. 4, 2007

(30) Foreign Application Priority Data

Apr. 30, 2004 (JP) ............................. 2004-135183
May 26, 2004 (JP) ............................. 2004-184296
Dec. 24, 2004 (JP) ............................. 2004-373564

(51) Int. Cl.
*A61K 36/537* (2006.01)
(52) U.S. Cl. .................................................. 424/746
(58) Field of Classification Search ................ None
See application file for complete search history.

(56) References Cited

U.S. PATENT DOCUMENTS

| 6,123,945 | A | 9/2000 | Nakatsu et al. |
| 6,331,551 | B1 | 12/2001 | Subbiah |
| 2005/0004217 | A1 | 1/2005 | Yamamoto et al. |

FOREIGN PATENT DOCUMENTS

| EP | 0 296 564 A2 | 12/1988 |
| FR | 2 856 299 A1 | 12/2004 |
| JP | 6-072855 A | 3/1994 |
| JP | 09-118798 | * 11/1998 |
| JP | 10-298070 A | 11/1998 |
| JP | 2000-073057 A | 3/2000 |
| JP | 3236130 B2 | 9/2001 |
| WO | WO 01/74327 A1 | 10/2001 |

OTHER PUBLICATIONS

Tsukahara et al. Inhibitory Effect of an Extract of Sanguisorba Officinalis L. on Ultraviolet-B-Induced Photodamage of Rat Skin. Biol. Pharm. Bull. 24 (9) 998-103. 2001.*
Ethylene. Retrieved from the internet. Jan. 4, 2004. <http://web.archive.org/web/20040124005856/http://en.wikipedia.org/wiki/Ethylene>. Retrieved on Aug. 22, 2008.*
Hilton. Consumers Ill-Informed About Anti-Aging Options. Dermatology Times. Jul. 2004. 25:7. pp. 58 and 61.*
Y. Hamada et al., "Vitamin A and its Derivatives as an Antiwrinkle Material," Fragrance Journal, vol. 26, No. 4, Apr. 15, 1998, pp. 75-77.
M. Itoh, "Application of Lamiaceae Plants to Cosmetics—Focusing Primarily on Motherwort," Fragrance Journal, vol. 29, No. 5, May 15, 2001, pp. 77-80.
D.L. Bissett et al., "An Animal Model of Solar-Aged Skin: Histological, Physical, and Visible Changes in UV-Irradiated Hairless Mouse Skin,:" Photochemistry and Photobiology, vol. 46, No. 3, 1987, pp. 367-378.

* cited by examiner

*Primary Examiner*—Patricia Leith
*Assistant Examiner*—Melenie McCormick
(74) *Attorney, Agent, or Firm*—Foley & Lardner LLP

(57) ABSTRACT

The present invention provides an antiwrinkle agent and skin cosmetic composition having excellent alleviating effects on wrinkles appearing due to aging, and especially at exposed locations of skin, and a high degree of safety.

The present invention relates to an antiwrinkle agent and skin cosmetic composition comprising a sclareol derivative represented by the following structural formula (1).

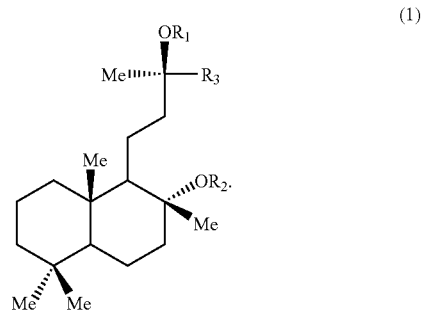

(1)

3 Claims, 4 Drawing Sheets

ANTIWRINKLE AGENT AND SKIN COSMETIC COMPOSITION

TECHNICAL FIELD

The present invention relates to an antiwrinkle agent and skin cosmetic composition having an excellent alleviating effect on wrinkles formed due to aging, especially at locations of exposed skin, and a high degree of safety.

BACKGROUND ART

The organs of all living beings, including humans, gradually deteriorate with age following birth and growth, their functions eventually stop, and once those portions of organs for which functions have stopped reach a certain point, death occurs. The process by which function gradually deteriorates is referred to as aging. Since the skin is directly subjected to the effects of the surrounding environment, and has an important function for maintaining the environment within the body, although it rarely completely loses its function, it is susceptible to the appearance of signs of aging such as wrinkles, spots, darkening and looseness, and this is particularly prominent at locations of the skin exposed to sunlight.

As aging of the skin progresses, its defense against stimulation such as oxidation stress weakens. This causes a disturbance in the skin's internal environment, which further promotes aging. At exposed portions of the skin in particular, since these locations are continuously exposed to ultraviolet radiation and other forms of strong oxidation stress, the progress of aging is remarkable. This type of change in the skin is referred to as photoaging, and skin affected in this manner demonstrates thickening of the epidermis, and a reduction in collagen which is a major constituent of the dermis. Consequently, an aesthetically displeasing state results such as the formation of deep, large wrinkles.

Although retinoic acid is used as a prescription drug in the United States as a substance having alleviating effects on wrinkles formed as a result of the progression of photoaging, due to strong adverse side effects and problems with safety, it has not been approved in Japan (see non-patent document 1). Thus, there is a need for an antiwrinkle substance having a high degree of safety and adequate effects.

On the other hand, sclareol is a diterpene alcohol represented by the following formula (2), and is obtained from extracts and refined oils such as *Salvia sclarea*, which is a member of the lamiaceae family of plants which are easily cultivated. Since sclareol has a structure similar to female hormone (estrogen) and has excellent hormone regulatory action, it is applied in aroma therapy and other aroma fields (see non-patent document 2). In addition, although an agent which inhibits melanin production due to sclareol formulated therein have been proposed (see patent document 1), there have not been any studies conducted on its safety during application or on its wrinkles alleviating effects.

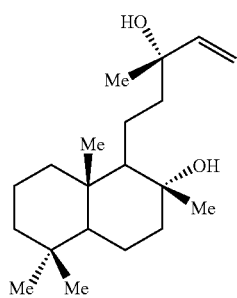

(2)

Therefore, as a result of extensive studies conducted by the inventors of the present invention, it was clearly determined that sclareol has skin sensitizing properties. Namely, sclareol was found to have problems with safety depending on the amount formulated into skin cosmetic composition.

patent document 1: Japanese Patent Publication No. 3236130 non-patent document 1: Hamada, Y. and Fukuse H.: "Vitamin A and its Derivatives as an Antiwrinkle Material", Fragrance Journal, Fragrance Journal Publishing Co., Ltd., Apr. 15, 1998, Vol. 26, No. 4, pp. 75-77 non-patent document 2: Itoh, M.: "Application of Lamiaceae Plants to Cosmetics—Focusing Primarily on motherwort", Fragrance Journal, Fragrance Journal Publishing Co., Ltd., May 15, 2001, Vol. 29, No. 5, pp. 77-80

DISCLOSURE OF THE INVENTION

Problems to be Solved by the Invention

An object of the present invention is to provide an antiwrinkle agent and skin cosmetic composition having excellent alleviating effects on wrinkles appearing due to aging, and especially at exposed locations of skin, and a high degree of safety.

Means for Solving the Problems

As a result of conducting extensive studies in consideration of the above circumstances, the inventors of the present invention confirmed that specific sclareol derivatives, particularly a hydrogenated sclareol obtained by reducing an alkenyl group of sclareol, and an acylated sclareol obtained by acylating at least one of hydroxyl group of sclareol, has superior safety as compared with sclareol, and a skin cosmetic composition formulated therewith has excellent safety and excellent wrinkle alleviating effects, thereby leading to completion of the present invention.

Namely, claim 1 of the present invention relates to an antiwrinkle agent comprising a sclareol derivative represented by formula (1):

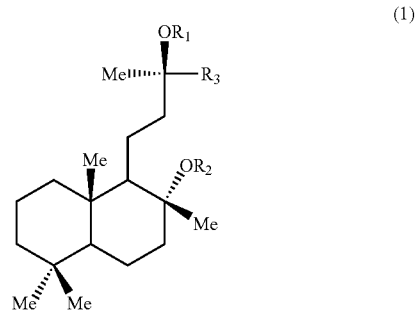

(1)

(wherein, $R_1$ and $R_2$ independently represent a hydrogen atom, or a linear or branched, saturated or unsaturated acyl group having 2 to 12 carbon atoms, $R_3$ represents an ethyl group in the case $R_1$ and $R_2$ both represent hydrogen atoms, and $R_3$ represents an ethenyl group in the case of at least one of $R_1$ and $R_2$ represents the acyl group).

In addition, claim 2 of the present invention relates to an antiwrinkle agent comprising a sclareol derivative of formula (1) according to claim 1, wherein $R_1$ and $R_2$ both represent hydrogen atoms, and $R_3$ represents an ethyl group.

In addition, claim 3 of the present invention relates to an antiwrinkle agent comprising a sclareol derivative of formula (1) according to claim 1, wherein $R_1$ and $R_2$ independently represent a hydrogen atom, or a linear or branched, saturated or unsaturated acyl group having 2 to 12 carbon atoms, at least one of $R_1$ and $R_2$ represents the acyl group, and $R_3$ represents an ethenyl group.

In addition, claim 4 of the present invention relates to an antiwrinkle agent according to claim 2, which is obtained by hydrogenating an extract of *Salvia sclarea*, Lamiaceae.

In addition, claim 5 of the present invention relates to an antiwrinkle agent according to claim 3, which is obtained by acylating an extract of *Salvia sclarea*, Lamiaceae.

Moreover, claim 6 of the present invention relates to a skin cosmetic composition comprising a sclareol derivative represented by formula (1):

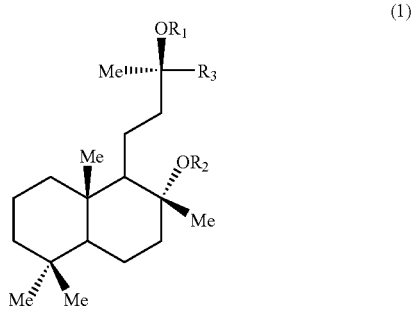

(1)

(wherein, $R_1$ and $R_2$ independently represent a hydrogen atom, or a linear or branched, saturated or unsaturated acyl group having 2 to 12 carbon atoms, $R_3$ represents an ethyl group in the case $R_1$ and $R_2$ both represent hydrogen atoms, and $R_3$ represents an ethenyl group in the case of at least one of $R_1$ and $R_2$ represents the acyl group).

Moreover, claim 7 of the present invention relates to a skin cosmetic composition comprising a sclareol derivative of formula (1) according to claim 6, wherein $R_1$ and $R_2$ both represent hydrogen atoms, and $R_3$ represents an ethyl group.

Moreover, claim 8 of the present invention relates to a skin cosmetic composition comprising a sclareol derivative of formula (1) according to claim 6, wherein $R_1$ and $R_2$ independently represent a hydrogen atom, or a linear or branched, saturated or unsaturated acyl group having 2 to 12 carbon atoms, at least one of $R_1$ and $R_2$ represents the acyl group, and $R_3$ represents an ethenyl group.

Moreover, claim 9 of the present invention relates to a skin cosmetic composition according to claim 7, which is obtained by hydrogenating an extract of *Salvia sclarea*, Lamiaceae.

In addition, claim 10 of the present invention relates to a skin cosmetic composition according to claim 8, which is obtained by acylating an extract of *Salvia sclarea*, Lamiaceae.

EFFECTS OF THE INVENTION

The present invention is able to provide an antiwrinkle agent and skin cosmetic composition which has excellent alleviating effects on wrinkles formed due to aging, especially at locations of exposed skin, and is capable of maintaining the skin in a dermatologically and aesthetically healthy state.

BEST MODE FOR CARRYING OUT THE INVENTION

Figure 1:
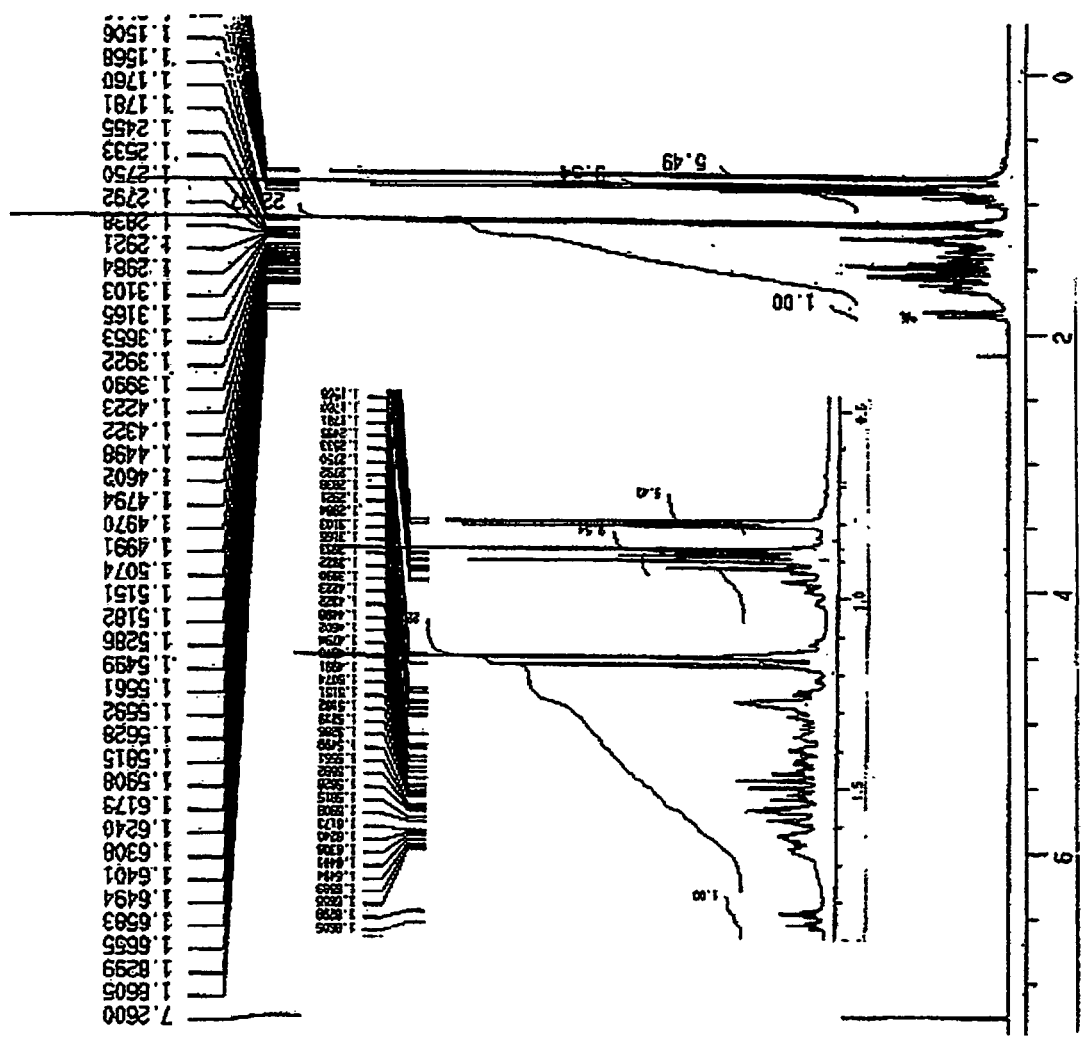
FIG. 1 shows the $^1$H-NMR spectrum of hydrogenated sclareol described in Production Example 1.

The following provides a detailed description of embodiments of the present invention.

A sclareol derivative represented by formula (1) used in the present invention can be obtained by reducing the alkenyl group of a commercially available sclareol manufactured by Tokyo Chemical Industry Co., Ltd. or Sigma-Aldrich Co., Ltd. using palladium carbon, or by acylating using an acid chloride or acid anhydride. In addition, a natural extract containing a large amount of sclareol, such as an extract of *Salvia sclarea*, can be used directly after reducing or acylating.

The *Salvia sclarea* extract used in the present invention may be from the whole plant, leaves, flowers, stem, root or any other site of *Salvia sclarea*, and can be obtained by extracting the above with a solvent such as liquefied gas (such as liquefied carbonic acid, liquefied propane or liquefied butane), water, lower alcohols having 1 to 5 carbon atoms (such as methyl alcohol, ethyl alcohol or propyl alcohol), water-containing lower alcohols, esters of lower alcohols having 1 to 5 carbon atoms and fatty acids having 1 to 5 carbon atoms (such as methyl acetate, ethyl acetate or butyl acetate), ketones (such as acetone or methyl ethyl ketone), water-containing forms of the aforementioned esters and ketones, halogenated hydrocarbons (such as chloroform, dichloromethane, dichloroethane or trichloroethane), ethers (such as methyl ether, ethyl ether, tetrahydrofuran or dioxane), hydrocarbons (such as petroleum ether or hexane) or mixtures of the aforementioned solvents; the resulting extract can be used directly, or after concentration.

There are no particular limitations on the extraction method, and examples of such methods include immersing the raw material plant in a solvent at room temperature for about 1 to 100 hours, and extracting while heating and stirring at a temperature equal to or below the boiling point of the solvent. There are no particular limitations on the amount of solvent used, and may be, for example, 1 to 100 times, and preferably 5 to 50 times, the raw material plant in terms of the weight ratio. In addition, refined oils obtained by steam distillation can also be used.

In particular, a *Salvia sclarea* extract obtained by extracting the leaves, flowers or whole plant of *Salvia sclarea* with a hydrocarbon such as petroleum ether or hexane is preferably used in the present invention, while that treated with a lower alcohol having 1 to 5 carbon atoms following extraction is also preferable. More specifically, a concrete or absolute commonly used in the fragrance industry is used preferably. A concrete is obtained by, for example, charging a flower and a purified solvent (such as petroleum ether or hexane) into an extractor and immersing at room temperature to transfer the fragrance of flower followed by removing the treated flower and removing the solvent under reduced pressure. An absolute is obtained by, for example, re-extracting a concrete by heating and dissolving in highly pure ethyl alcohol, cooling the solvent to, for example, −15 to 25° C., and removing wax and other insoluble matters followed by distilling off the ethyl alcohol under reduced pressure.

A sclareol derivative particularly used in the present invention is a hydrogenated sclareol represented by the following formula (3):

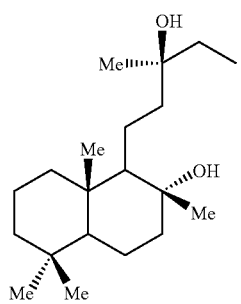

(3)

which can be obtained by reducing the alkenyl group of a commercially available sclareol or a natural extract containing a large amount of sclareol such as a *Salvia sclarea* extract, using palladium carbon and the like.

In addition, a sclareol derivative particularly used in the present invention is an acylated sclareol represented by the following formula (4):

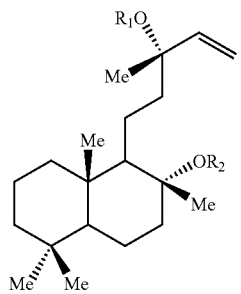

(4)

which can be obtained by acylating a commercially available sclareol or natural extract containing a large amount of sclareol such as a *Salvia sclarea* extract, using an acid chloride or acid anhydride, and in the aforementioned formula, $R_1$ and $R_2$ independently represent a hydrogen atom, or a linear or branched, saturated or unsaturated acyl group having 2 to 12 carbon atoms, provided $R_1$ and $R_2$ are not both hydrogen atoms.

An example of an acylated sclareol represented by formula (4) is an acylated sclareol represented by the following formula (5):

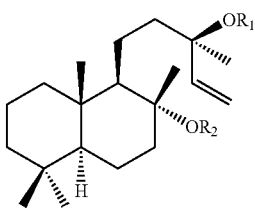

(5)

wherein, $R_1$ and $R_2$ independently represent a hydrogen atom, or a linear or branched, saturated or unsaturated acyl group having 2 to 12 carbon atoms, provided $R_1$ and $R_2$ are not both hydrogen atoms.

The acylated sclareol represented by formula (4) may be a monoacylated sclareol or a diacylated sclareol, and in the case of a diacyl form, the two acyl groups may be the same or different. A monoacylated sclareol is more preferable.

Examples of linear or branched, saturated or unsaturated acyl groups having 2 to 12 carbon atoms include linear or branched saturated acyl groups such as an acetyl group, propionyl group, butyryl group, isobutyryl group, valeryl group, isovaleryl group, pivaloyl group, hexanoyl group, octanoyl group or lauroyl group; and, linear or branched unsaturated acyl groups such as an acryloyl group, methacryloyl group or crotonyl group. A linear or branched saturated acyl group having 2 to 8 carbon atoms is preferable, an acetyl group, hexanoyl group or octanoyl group is more preferable, and an acetyl group is particularly preferable.

The amount of a sclareol derivative formulated in the present invention is preferably 0.001 to 10% by weight (hereinafter, to be simply referred to as %) based on the total amount of antiwrinkle agent or skin cosmetic composition. If the amount is below the lower limit, the target effects of the present invention are inadequate, and if the amount is exceeded, improvement of effects corresponding to the increased amount are not obtained, thereby making this unpreferable. Thus, the amount of sclareol derivative formulated in the present invention is preferably 0.01 to 8.0% and particularly preferably 0.1 to 5.0%. Furthermore, in the case of using a sclareol derivative obtained from a *Salvia sclarea* extract in an antiwrinkle agent or skin cosmetic composition of the present invention without isolating, the amount of sclareol derivative contained therein is formulated so as to be within the aforementioned range.

An antiwrinkle agent of the present invention can be formulated in a skin cosmetic composition or external drug preparation in a prescription drug, over-the-counter drug or bath salts and the like, and examples of the drug form thereof include a lotion, emulsion, cream or pack.

Furthermore, in addition to the aforementioned components, a coloring agent, fragrance, preservative, surfactant, pigment or antioxidant can be appropriately formulated into the antiwrinkle agent or skin cosmetic composition of the present invention within a range which achieves the object of the present invention.

EXAMPLES

The following provides a detailed description of the present invention based on examples and comparative examples thereof.

Production Example 1

Production Example of Hydrogenated Sclareol 1.5 g of sclareol (Sigma-Aldrich, Cat. No. 35,799-5) were dissolved in 50 mL of ethanol, and 500 mg of palladium carbon (5% palladium) were added to this solution followed by stirring overnight in a hydrogen atmosphere (normal pressure) at room temperature. After filtering out the insoluble matter, the filtrate was concentrated under reduced pressure to obtain 1.2 g of a hydrogenated sclareol used in the present invention.

According to the results of $^1$H-NMR of the hydrogenated sclareol, olefin signals observed at 5.03 ppm (dd, J=10.8, 1.2 Hz), 5.21 ppm (dd, J=17.2, 1.4 Hz) and 5.94 ppm (dd, J=17.4, 10.8 Hz) had disappeared, and a methyl signal resulting from olefin reduction was confirmed at 0.90 ppm (t, 3H) in $^1$H-NMR. The $^1$H-NMR spectrum of the resulting hydrogenated sclareol is shown in FIG. 1.

Figure 2:
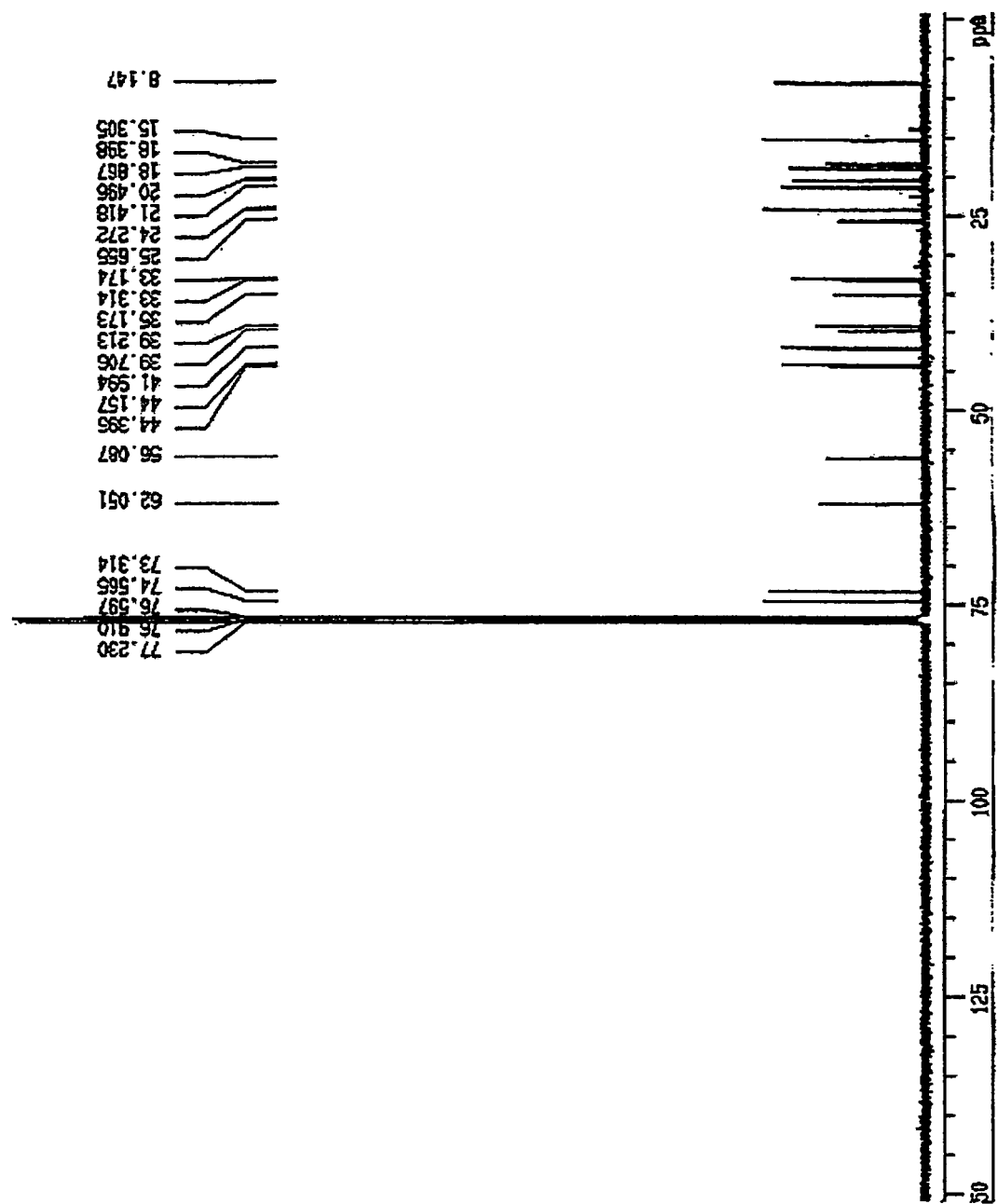
FIG. 2 shows the $^{13}$C-NMR spectrum of hydrogenated sclareol described in Production Example 1.

According to the results of $^{13}$C-NMR of the hydrogenated sclareol, olefin signals observed at 111 ppm and 146 ppm had disappeared, and methyl and methylene signals resulting from olefin reduction were confirmed at 8.15 ppm and 35.1 ppm, respectively, in $^{13}$C-NMR. The $^{13}$C-NMR spectrum of the resulting hydrogenated sclareol is shown in FIG. 2.

Production Example 2

Production Example of Hydrogenated Sclareol Using *Salvia sclarea* Concrete 10 g of *Salvia sclarea* concrete were dissolved in 500 mL of ethanol, and 3.5 g of palladium carbon (5% palladium) were added to this solution followed by stirring overnight in a hydrogen atmosphere (normal pressure) at room temperature. After filtering out the insoluble matter, the filtrate was concentrated under reduced pressure to obtain 8 g of a hydrogenated *Salvia sclarea* (containing about 70 to 80% hydrogenated sclareol).

Production Example 3

Production Example of Acylated Sclareol 1.5 g of sclareol (Sigma-Aldrich, Cat. No. 35,799-5) were dissolved in 10 mL of acetic anhydride, and pyridine was added dropwise into the solution followed by stirring overnight at room temperature. After washing the insoluble matter by water, the solution was extracted with ethyl acetate and dried. The extract was fractionated into fractions having rf values of 0.86 and 0.40 in thin-layer chromatography (developing solvent: hexane/ethyl acetate=6/1) by column chromatography (hexane/ethyl acetate=8/1 to 4/1), followed by concentrating under reduced pressure to obtain sclareol derivatives used in the present invention in the form of 0.5 g of a diacetylated sclareol and 0.6 g of monoacylated sclareol (isomer mixture), respectively, as white crystals.

Figure 3:
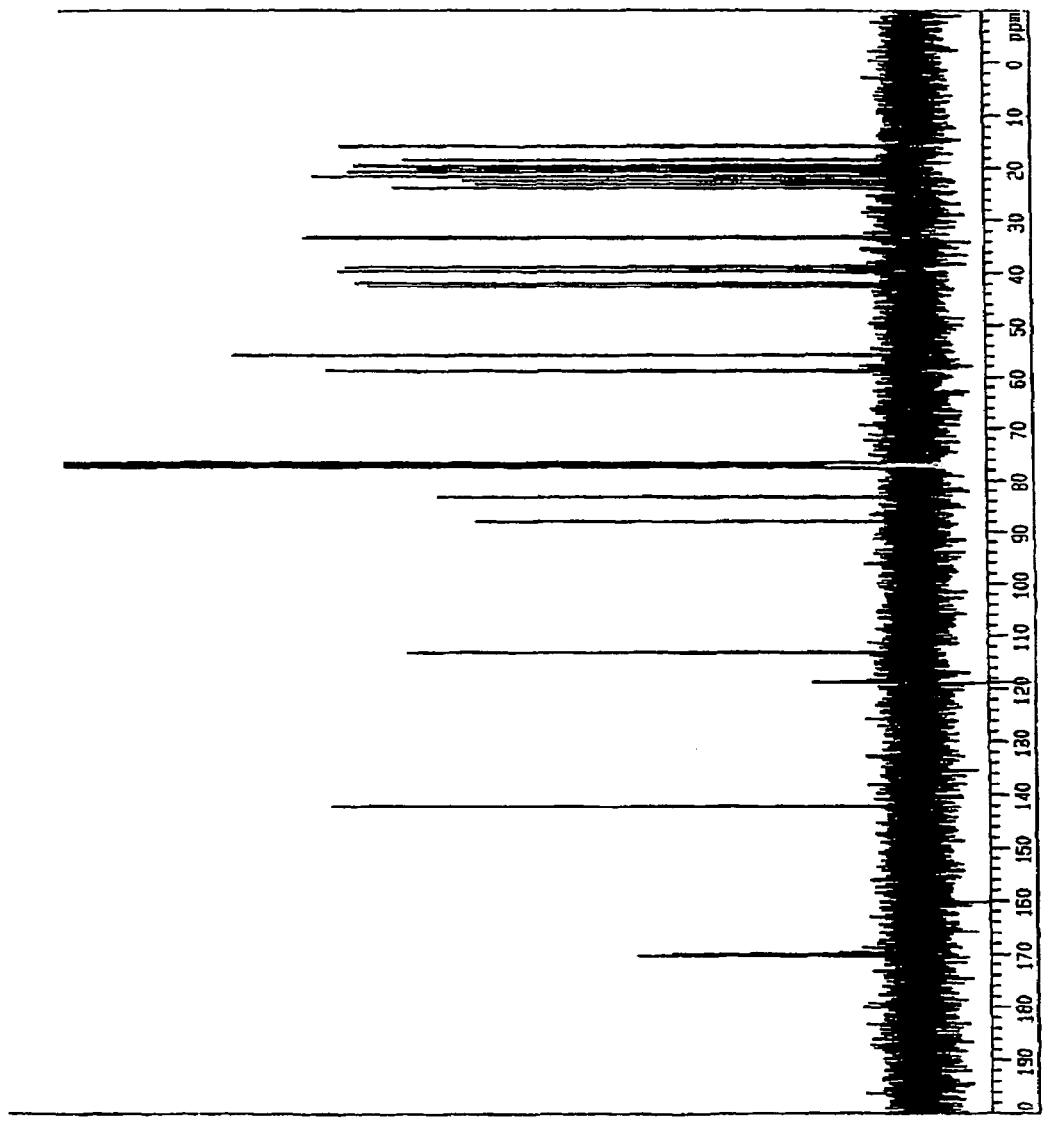
FIG. 3 shows the $^{13}$C-NMR spectrum of a diacetylated sclareol described in Production Example 3.

According to the results of $^{13}$C-NMR of the diacetylated sclareol, the signals observed at 73.6 ppm and 74.7 ppm for sclareol had disappeared, and signals resulting from substitution by the acetyl groups were confirmed at 83.3 ppm and 87.9 ppm. In addition, signals indicating carbonyl groups were newly confirmed at 169.7 ppm and 170.2 ppm. The $^{13}$C-NMR spectrum of the resulting diacetylated sclareol is shown in FIG. 3.

Figure 4:
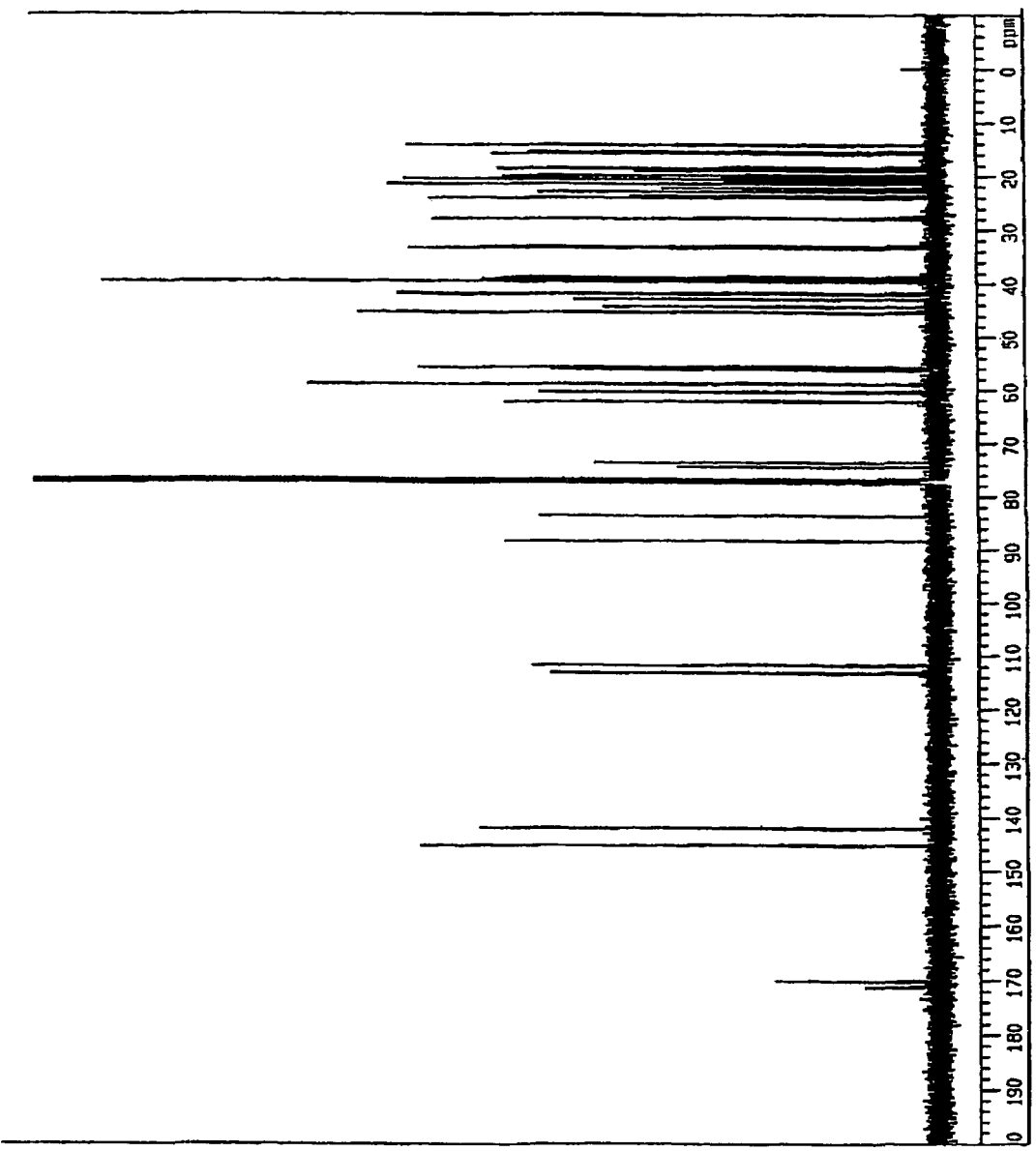
FIG. 4 shows the $^{13}$C-NMR spectrum of a monoacetylated sclareol (isomer mixture) described in Production Example 3.

Since a similar $^{13}$C-NMR spectrum was obtained for the monoacetylated sclareol (isomer mixture) in which the disappearance of signals and appearance of new signals indicating hydroxyl group acetylation was confirmed, the formation of this derivative was confirmed. The $^{13}$C-NMR spectrum of the sclareol monoacetyl form (isomer mixture) is shown in FIG. 4.

Production Example 4

Production Example of Sclareol Acyl Forms Using *Salvia sclarea* Concrete 10 g of *Salvia sclarea* concrete were dissolved in 100 mL of acetic anhydride, and pyridine was added dropwise into this solution followed by stirring overnight at room temperature. After washing the insoluble matter by water, the solution was extracted with ethyl acetate and dried. The extract was fractionated into fractions having rf values of 0.86 and 0.40 in thin-layer chromatography (developing solvent: hexane/ethyl acetate=6/1) by column chromatography (hexane/ethyl acetate=8/1 to 4/1) and concentrating under reduced pressure to obtain 3.4 g and 4.0 g of a diacetylated *Salvia Sclarea* and monoacetylated *Salvia Sclarea* (isomer mixture), respectively, as white crystals.

Test Example 1

Safety Test of Sclareol Derivatives and Sclareol

Safety (sensitization) was evaluated using a maximization test.

An area of the skin over the scapula measuring 4×6 cm$^2$ was shaved in Hartley guinea pigs (females) having body weights of 350 to 400 g, and two rows of three intradermal injections per row were made in the order indicated below.

1) 0.05 mL aliquots of Freund's complete adjuvant (hereinafter, to abbreviated as FCA solution) were intradermally injected at two locations on the left and right sides.

2) 0.05 mL aliquots of an olive oil solution containing 10% of a sclareol derivative obtained in the aforementioned producing examples or sclareol were intradermally injected at two locations on the left and right sides.

3) 0.05 mL aliquots of an emulsified solution obtained by adding an equal volume of sterile water to an FCA solution containing 20% sclareol or sclareol derivative obtained in the aforementioned production examples were intradermally injected at two locations on the left and right sides.

The same sites on the animals were shaved one week after these procedures, and vaseline containing 10% sodium lauryl sulfate was rubbed onto the skin to induce mild inflammation. 24 hours after rubbing, 0.2 mL of olive oil solutions containing 10% sclareol derivative sample of the present invention or sclareol were applied to a piece of gauze, which was then affixed to cover the skin for 48 hours. The abdomens of the animals were shaved on the 21st day after intradermal injection, and olive oil solutions containing 5% and 10% of a sclareol derivative sample of the present invention, or an olive oil solution containing 5% of a sclareol sample were affixed to cover the skin for 24 hours. Evaluations were made macroscopically 24 and 48 hours later in accordance with the evaluation criteria shown in Table 1.

TABLE 1

| Symptom | Score |
| --- | --- |
| No macroscopic changes | 0 |
| Mild or diffuse erythema | 1 |
| Moderate erythema | 2 |
| Severe erythema | 3 |

As a result, in contrast to sensitization being confirmed for sclareol, sensitization was not confirmed for the sclareol derivatives of the present invention as shown in Table 2.

TABLE 2

| | | Time of Evaluation | |
| --- | --- | --- | --- |
| Compound | Concentration (%) | After 24 Hours PR, (MR) | After 48 Hours PR, (MR) |
| Hydrogenated sclareol | 5 | 0, (0) | 0, (0) |
| (Production Example 1) | 10 | 0, (0) | 0, (0) |
| Monoacetylated sclareol | 5 | 0, (0) | 0, (0) |
| (isomer mixture, | 10 | 0, (0) | 0, (0) |
| Production Example 3) | | | |
| Diacetylated sclareol | 5 | 0, (0) | 0, (0) |

TABLE 2-continued

| Compound | Concentration (%) | Time of Evaluation | |
| --- | --- | --- | --- |
| | | After 24 Hours PR, (MR) | After 48 Hours PR, (MR) |
| (Production Example 3) | 10 | 0, (0) | 0, (0) |
| Sclareol | 5 | 4/10, (0.4) | 4/10, (0.4) |

PR: Sensitization rate (Number of positive animals/Number of animals used)
MR: Mean score (average of reaction scores)

According to the results of this test, the sclareol derivatives of the present invention were determined to clearly demonstrate a high degree of safety as compared with sclareol.

Test Example 2

Wrinkle Alleviation Test of Sclareol Derivatives

Wrinkle alleviating effects when a sample containing base only or a sample containing a sclareol derivative of the present invention was applied to photoaged skin were examined by the following test method.

1. Experimental Animals

Hairless mice (age 10 weeks at the start of the test) were used in groups of 10 animals each.

2. Measurement of Wrinkle Alleviating Effect 2-1. Photoaging Conditions and Measurement Method Photoaging was induced by irradiating the mice with UVA and UVB once a day, 5 times a week for 8 weeks. The radiation doses for UVA were increased each week for the first three weeks in the order of 20 J/cm$^2$, 25 J/cm$^2$ and 30 J/cm$^2$, the radiation doses for UVB were increased each week for the first three weeks in the order of 20 mJ/cm$^2$, mJ/cm$^2$ and 40 mJ/cm$^2$, and the animals were irradiated at the maximum respective dose starting in the 3rd week.

Wrinkle alleviating effect was evaluated according to the wrinkle score and dermis collagen content. The wrinkle score was determined according to the method of Bissett et al. (Photochem. Photobiol. 46: 367-368, 1987). Namely, the overall size and depth of wrinkles were evaluated macroscopically, and scored based on a maximum score of 3 by assigning a score of 3 when "large, deep wrinkles can be confirmed", a score of 2 when "some wrinkles can be confirmed", a score of 1 when "wrinkles cannot be confirmed", and a score of 0 when "normal, fine skin is observed".

Dermis collagen content was measured by collecting a sample of whole skin and homogenizing with a Polytron Homogenizer (KINEMATICA AG), followed by extracting the collagen fraction, subjecting to acid hydrolysis and measuring the hydroxyproline content as the amount of collagen using an amino acid analyzer (JASCO Corp.).

2-2. Samples and Experiment Method

Samples were prepared by blending 1% of the hydrogenated sclareol obtained in Production Example 1, and the monoacetylated sclareol (isomer mixture) and diacetylated sclareol obtained in Production Example 3, respectively, in a 50% ethanol solution (base) (Examples 1 to 3). A sample containing base only was also prepared and designated as Comparative Example 1.

First, 0.1 mL of each sample was applied to the skin on the backs of the hairless mice (diameter: about 2.5 cm) at a frequency of once a day, 5 times a week starting in the 5th week after the start of UV irradiation though the 4th week following termination of UV irradiation. Wrinkle scores were evaluated after the final application, after which the animals were sacrificed and skin samples were collected. Collagen content was determined by calculating the amount of hydroxyproline per square centimeter. The wrinkle scores and collagen contents were compared with the base applied group serving as a control.

(Wrinkle Score Evaluation Results 1)

| Group | Wrinkle Score |
| --- | --- |
| Example 1 Hydrogenated sclareol sample applied group | 2.40 ± 0.11 |
| Comparative Example 1 Base sample applied group | 2.70 ± 0.09 |

(Values are indicated as the average ± standard error)

(Wrinkle Score Evaluation Results 2)

| Group | Wrinkle Score |
| --- | --- |
| Example 2 Monoacetylated sclareol sample applied group | 2.45 ± 0.08 |
| Example 3 Diacetylated sclareol sample applied group | 2.55 ± 0.05 |
| Comparative Example 1 Base sample applied group | 2.75 ± 0.08 |

(Values are indicated as the average ± standard error)

Example 1 to 3 demonstrated significantly lower wrinkle scores than Comparative Example 1, thus indicating that the sclareol derivatives of the present invention are effective against wrinkles caused by photoaging.

(Collagen Content Measurement Results 1)

| Group | Collagen Content (μmol/L) |
| --- | --- |
| Example 1 Hydrogenated sclareol sample applied group | 7.72 ± 0.49 |
| Comparative Example 1 Base sample applied group | 6.91 ± 0.48 |

(Values are indicated as the average ± standard error)

(Collagen Content Measurement Results 2)

| Group | Collagen Content (μmol/L) |
| --- | --- |
| Example 2 Monoacetylated sclareol sample applied group | 8.75 ± 0.50 |
| Comparative Example 1 Base sample applied group | 7.62 ± 0.29 |

(Values are indicated as the average ± standard error)

As indicated by collagen content measurements results 1 and 2, Examples 1 and 2 demonstrated an increasing trend in collagen content as compared with Comparative Example 1. Namely, the sclareol derivatives of the present invention were demonstrated to be effective against reduced dermis collagen levels caused by photoaging.

On the basis of the results of this test, the sclareol derivatives of the present invention were found to clearly have alleviating effects on wrinkles caused by photoaging as compared with Comparative Example 1.

Examples 4 and 5 and Comparative Example 2

In these examples and comparative example, skin lotions having the compositions indicated below were prepared according to the following preparation method, and samples of these skin lotions were evaluated for wrinkle alleviating effect according to the following procedure.

Skin lotions of the examples and comparative example were applied to the skin of five healthy adult panelists each (women age 42 to 56) having wrinkles at the corners of their eyes. The women then filled in a questionnaire relating to the condition of the skin (wrinkles) at the corners of their eyes using the method described below.

Each sample was applied to the area of wrinkled skin in the corner of the left or right eye in about 0.2 mL aliquots twice a day in the morning after washing the face and evening after bathing each day for 2 months (60 days) (each sample was applied over an area of 2×2 cm, or about 4 cm$^2$, centering around the wrinkled area in the corner of the selected eye). Next, the panelists filled in the questionnaire regarding the condition of the skin (wrinkles) in the corner of the selected eye after the final application.

Skin Lotion Composition

| Ingredients | Blended Amt. (%) Example 4 | Example 5 |
|---|---|---|
| Ingredient A | | |
| Olive oil | 10.0 | 10.0 |
| Isopropyl myristate | 1.0 | 1.0 |
| Polyoxyethylene (20) sorbitan monolaurate | 0.5 | 0.5 |
| Propylene glycol | 1.0 | 1.0 |
| Glycerol | 2.0 | 2.0 |
| Ingredient B | | |
| Methyl paraben | 0.1 | 0.1 |
| Ethanol | 7.0 | 7.0 |
| Purified water | Remainder to bring to a total of 100 | Remainder to bring to a total of 100 |
| Ingredient C | | |
| Hydrogenated sclareol | 1.0 | |
| Dioctanoylated sclareol | | 1.0 or 0 (Comparative Example 2) |

Preparation Method:

In each example, the sclareol derivative of ingredient C was added to ingredient B, and after uniformly mixing, ingredient A was added and dispersed by stirring followed by filling into a container. The contents were uniformly dispersed by shaking at the time of use. Furthermore, the hydrogenated sclareol of ingredient C was obtained in the aforementioned Production Example 1. On the other hand, the dioctanoylated sclareol was obtained by using, for example, octanoyl chloride instead of acetic anhydride according to the same method as that used in the aforementioned Production Example 3.

On the basis of the questionnaire results, the numbers of panelists who replied that the skin lotion of Example 4 was more effective than that of Comparative Example 2 for each of the items relating to skin (wrinkle) condition are shown below.

| Item | Number of Panelists |
|---|---|
| Wrinkles no longer conspicuous | 5 |
| Skin became softer | 4 |
| Skin became tighter | 5 |
| Skin exhibited luster | 4 |
| Skin tone became brighter | 3 |

Similarly, the numbers of panelists who replied that the skin lotion of Example 5 was more effective than the skin lotion of Comparative Example 2 for each of the items relating to skin (wrinkle) condition on the basis of the questionnaire results are shown below.

| Item | Number of Panelists |
|---|---|
| Wrinkles no longer conspicuous | 5 |
| Skin became softer | 5 |
| Skin became tighter | 5 |
| Skin exhibited luster | 4 |
| Skin tone became brighter | 3 |

On the basis of the results of this test, the skin lotions of Examples 4 and 5 clearly alleviated wrinkles as compared with Comparative Example 2, and flexibility and skin tension, which become worse due to photoaging, were also determined to be alleviated. In addition, there were no skin abnormalities such as irritation or itching observed due to use of the skin lotions of the present invention.

Examples 6 to 10

Skin creams having the following compositions were prepared according to the preparation method described below and a questionnaire survey was conducted by having 20 healthy adult panelists (women age 45 to 56) suffering from wrinkles in the corners of their eyes use the skin creams for 1 week or more prior to the survey.

TABLE 10

| | Composition Blended Amount % | | | | |
|---|---|---|---|---|---|
| Ingredients | Example 6 | Example 7 | Example 8 | Example 9 | Example 10 |
| Ingredient A | | | | | |
| Bees wax | 2.0 | 2.0 | 2.0 | 2.0 | 2.0 |
| Stearic acid | 5.0 | 5.0 | 5.0 | 5.0 | 5.0 |

TABLE 10-continued

| | Composition | | | | |
|---|---|---|---|---|---|
| | Blended Amount % | | | | |
| Ingredients | Example 6 | Example 7 | Example 8 | Example 9 | Example 10 |
| Stearyl alcohol | 5.0 | 5.0 | 5.0 | 5.0 | 5.0 |
| Reduced lanolin | 2.0 | 2.0 | 2.0 | 2.0 | 2.0 |
| Squalene | 20.0 | 20.0 | 20.0 | 20.0 | 20.0 |
| Sorbitan monostearate | 3.0 | 3.0 | 3.0 | 3.0 | 3.0 |
| Polyoxyethylene (20) sorbitan monostearate | 3.0 | 3.0 | 3.0 | 3.0 | 3.0 |
| Propylene glycol | 5.0 | 5.0 | 5.0 | 5.0 | 5.0 |
| Ingredient B | | | | | |
| Methyl paraben | 0.2 | 0.2 | 0.2 | 0.2 | 0.2 |
| Purified water | Remainder to bring to a total of 100 | Remainder to bring to a total of 100 | Remainder to bring to a total of 100 | Remainder to bring to a total of 100 | Remainder to bring to a total of 100 |
| Ingredient C | | | | | |
| Hydrogenated sclareol | 1.0 | — | — | — | — |
| Hydrogenated salvia sclarea | — | 1.0 | — | — | — |
| Monohexanoylated sclareol (isomer mixture) | — | — | 1.0 | — | — |
| Diacetylated salvia sclarea | — | — | — | 1.0 | — |
| Monoacetylated salvia sclarea (isomer mixture) | — | — | — | — | 1.0 |

Preparation Method:

In each example, the sclareol derivative of ingredient C was added to ingredient B, and after melting each ingredient A and B by heating to 80° C. each, the ingredients were mixed and then cooled to 30° C. while stirring to prepare a skin cream. Furthermore, the hydrogenated sclareol of ingredient C was obtained in the aforementioned Production Example 1, the hydrogenated *Salvia sclarea* was obtained in the aforementioned Production Example 2, and the diacetylated *Salvia sclarea* and monoacetylated *Salvia sclarea* forms were obtained in Production Example 4. On the other hand, the monohexanoylated sclareol was obtained by using, for example, hexanoyl chloride instead of acetic anhydride according to the same method as that used in the aforementioned Production Example 3.

A questionnaire survey was conducted after having the panelists use the skin creams of Examples to 6 to 10. Those results are indicated below. The results show the number of panelists who replied in the affirmative with respect to after using the skin creams as compared with before using for each of the items shown, when replying to the following items contained in the questionnaire relating to wrinkle condition.

On the basis of the results of this test, the skin creams of Examples 6 to 10 were indicated as having alleviated wrinkles by making them no longer conspicuous as compared with prior to use by nearly all of the panelists. The factors behind these evaluations were determined that the skin creams were more effective in reducing the size of wrinkles rather than decreasing the numbers of wrinkles, thereby leading to alleviation of wrinkles caused by photoaging. In addition, there were no skin abnormalities such as irritation or itching observed due to use of the skin creams of the present invention.

INDUSTRIAL APPLICABILITY

An antiwrinkle agent of the present invention can be formulated to a skin cosmetic composition or external drug preparation in a prescription drug, over-the-counter drug or bath salts and so forth, can be in the form of, for example, a lotion, emulsion, cream or pack, and is extremely useful from the viewpoint of skin beauty.

The invention claimed is:
1. A method for reducing the appearance of wrinkles on a body comprising applying an effective amount of a composition including a sclareol derivative represented by formula (1):

TABLE 11

| | No. of Panelists | | | | |
|---|---|---|---|---|---|
| Item | Example 6 | Example 7 | Example 8 | Example 9 | Example 10 |
| Wrinkles no longer conspicuous | 17 | 15 | 18 | 16 | 18 |
| Wrinkles decreased in size | 18 | 15 | 18 | 17 | 17 |
| Wrinkles decreased in number | 6 | 6 | 6 | 6 | 6 |
| Wrinkles increased in number | 0 | 0 | 0 | 0 | 0 |

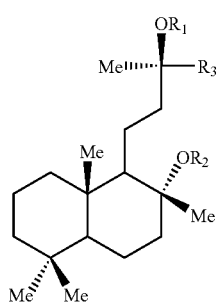

(1)

wherein, $R_1$ and $R_2$ independently represent a hydrogen atom, or a linear or branched, saturated or unsaturated acyl group having 2 to 12 carbon atoms, $R_3$ represents an ethyl group in the case $R_1$ and $R_2$ both represent hydrogen atoms, and $R_3$ represents an ethenyl group in the case of at least one of $R_1$ and $R_2$ represents the linear or branched, saturated or unsaturated acyl group, to skin of the body.

2. The method for reducing the appearance of wrinkles according to claim 1, wherein $R_1$ and $R_2$ both represent hydrogen atoms, and $R_3$ represents an ethyl group.

3. The method for reducing the appearance of wrinkles according to claim 2, wherein the sclareol derivative is obtained by hydrogenating an extract of *Salvia sclarea*, Lamiaceae.

* * * * *